(12) United States Patent
Plumptre

(10) Patent No.: US 9,457,150 B2
(45) Date of Patent: Oct. 4, 2016

(54) BIASING MECHANISM FOR A DRUG DELIVERY DEVICE

(75) Inventor: David Aubrey Plumptre, Worcestershire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 1177 days.

(21) Appl. No.: 12/788,692

(22) Filed: May 27, 2010

(65) Prior Publication Data
US 2010/0324497 A1    Dec. 23, 2010

Related U.S. Application Data

(60) Provisional application No. 61/182,825, filed on Jun. 1, 2009.

(30) Foreign Application Priority Data

Jul. 10, 2009    (EP) .................................... 09009051

(51) Int. Cl.
*A61M 5/00*    (2006.01)
*A61M 5/24*    (2006.01)
(Continued)

(52) U.S. Cl.
CPC ................ *A61M 5/24* (2013.01); *F16F 1/025* (2013.01); *A61M 5/31551* (2013.01); *A61M 2005/2407* (2013.01); *A61M 2005/2477* (2013.01);
(Continued)

(58) Field of Classification Search
CPC ......... A61M 5/24; A61M 2005/2407; A61M 2005/2492; A61M 5/31551; A61M 2005/2477; A61M 2005/2488; A61M 2005/2411; A61M 2005/2485; A61M 2005/2403; A61M 5/28; F16F 1/025
USPC ........ 604/207–211, 187, 110, 240, 232–235, 604/181
See application file for complete search history.

(56) References Cited

U.S. PATENT DOCUMENTS 3,302,462 A    2/1967  Pursell
4,879,567 A *  11/1989 Lawrence ................ 346/139 R
5,423,752 A    6/1995  Haber et al.
(Continued)

FOREIGN PATENT DOCUMENTS

DE    93 01 334 U1    4/1993
DE    197 30 999 C1    12/1998
(Continued)

OTHER PUBLICATIONS

Machine Deisgn, Penton Media, vol. 65, No. 11 (1993) p. 36 "Standard Compression Springs Save Space".

*Primary Examiner* — Bhisma Mehta
*Assistant Examiner* — Bradley G Thomas, Jr.
(74) *Attorney, Agent, or Firm* — McDonnell Boehnen Hulbert & Berghoff LLP

(57) ABSTRACT

A method and system for biasing a cartridge in a drug delivery device. An element for biasing a cartridge in a cartridge housing of a drug delivery device is provided. This non-plastic element does not comprise a coil spring. A self retained element for providing a spring bias to a cartridge in a cartridge holder of a drug delivery device comprises a first member having a shape that allows passage of a spindle of the drug delivery device. A portion of the first member is self retained by an internal surface of the drug delivery device. The self retained element biases the cartridge against an inner surface of the cartridge holder. This cartridge could be a removable cartridge.

12 Claims, 4 Drawing Sheets

(51) Int. Cl.
 *F16F 1/02* (2006.01)
 *A61M 5/315* (2006.01)

(52) U.S. Cl.
 CPC ............... *A61M2005/2488* (2013.01); *A61M 2005/2492* (2013.01); *Y10T 29/49826* (2015.01)

(56) References Cited

U.S. PATENT DOCUMENTS

| | | | |
|---|---|---|---|
| 5,514,097 | A | 5/1996 | Knauer |
| 5,584,815 | A | 12/1996 | Pawelka et al. |
| 5,591,136 | A | 1/1997 | Gabriel |
| 5,792,117 | A | 8/1998 | Brown |
| 5,820,602 | A | 10/1998 | Kovelman et al. |
| 5,925,021 | A * | 7/1999 | Castellano et al. ........... 604/207 |
| 6,090,080 | A | 7/2000 | Jost et al. |
| 6,936,032 | B1 | 8/2005 | Bush, Jr. et al. |
| 7,220,245 | B2 * | 5/2007 | Kriesel .......... 604/134 |
| 2002/0103471 | A1 * | 8/2002 | Granier .......... 604/506 |
| 2003/0218812 | A1 * | 11/2003 | Foote et al. ........... 359/874 |
| 2004/0127858 | A1 | 7/2004 | Bendek et al. |
| 2004/0162528 | A1 | 8/2004 | Horvath et al. |
| 2004/0186437 | A1 | 9/2004 | Frenette et al. |
| 2004/0210199 | A1 | 10/2004 | Atterbury et al. |
| 2004/0236285 | A1 | 11/2004 | Fisher et al. |
| 2005/0137571 | A1 | 6/2005 | Hommann |
| 2006/0153693 | A1 | 7/2006 | Fiechter et al. |
| 2006/0258988 | A1 | 11/2006 | Keitel et al. |
| 2007/0021718 | A1 * | 1/2007 | Burren .......... A61M 5/24 604/110 |
| 2008/0027397 | A1 | 1/2008 | DeRuntz et al. |
| 2008/0077095 | A1 | 3/2008 | Kirchhofer |
| 2008/0208123 | A1 | 8/2008 | Hommann |
| 2009/0227959 | A1 | 9/2009 | Hirschel et al. |

FOREIGN PATENT DOCUMENTS

| | | |
|---|---|---|
| DE | 298 18 721 U1 | 3/2000 |
| DE | 10 2005 063 311 A1 | 8/2006 |
| DE | 10 2005 060 928 A1 | 6/2007 |
| DE | 10 2006 038 123 A1 | 2/2008 |
| DE | 10 2007 026 083 A1 | 11/2008 |
| EP | 0 897 728 A1 | 2/1999 |
| EP | 0 937 471 A2 | 8/1999 |
| EP | 0 937 472 A2 | 8/1999 |
| EP | 1 541 185 A1 | 6/2005 |
| EP | 1 776 975 A2 | 4/2007 |
| EP | 1 923 084 A1 | 5/2008 |
| GB | 2 443 390 A | 5/2008 |
| WO | 92/18180 A1 | 10/1992 |
| WO | 93/07922 A1 | 4/1993 |
| WO | 96/23973 A1 | 8/1996 |
| WO | 96/39214 A1 | 12/1996 |
| WO | 97/10864 A1 | 3/1997 |
| WO | 99/03520 A1 | 1/1999 |
| WO | 9916487 A1 | 4/1999 |
| WO | 01/19434 A1 | 3/2001 |
| WO | 03/080160 A1 | 10/2003 |
| WO | 2004/020028 A1 | 3/2004 |
| WO | 2004/064902 A1 | 8/2004 |
| WO | 2004/078241 A1 | 9/2004 |
| WO | 2004/078242 A2 | 9/2004 |
| WO | 2004/078293 A1 | 9/2004 |
| WO | 2005/018721 A1 | 3/2005 |
| WO | 2005/021072 A1 | 3/2005 |
| WO | 2005/044346 A2 | 5/2005 |
| WO | 2005/123159 A2 | 12/2005 |
| WO | 2006/024461 A1 | 3/2006 |
| WO | 2006/058883 A2 | 6/2006 |
| WO | 2006/079481 A1 | 8/2006 |
| WO | 2006/089767 A1 | 8/2006 |
| WO | 2006/114395 A1 | 11/2006 |
| WO | 2006/125328 A1 | 11/2006 |
| WO | 2007/017052 A1 | 2/2007 |
| WO | 2007/067889 A1 | 6/2007 |
| WO | 2008/031235 A1 | 3/2008 |
| WO | 2008042285 A2 | 4/2008 |
| WO | 2008/074897 A1 | 6/2008 |
| WO | 2008/116766 A1 | 10/2008 |
| WO | 2008/128373 A1 | 10/2008 |

* cited by examiner

BIASING MECHANISM FOR A DRUG DELIVERY DEVICE

BACKGROUND

Field of the Present Patent Application

The present patent application is generally directed to drug delivery devices. More particularly, the present patent application is generally directed to drug delivery devices, such as pen type drug delivery devices. Such devices provide for self administration of medicinal product from a multi-dose cartridge and permit a user to set the delivery dose. The present application may find application in both resettable (i.e., reusable) and non-settable (i.e., non-reusable) type drug delivery devices.

However, aspects of the invention may be equally applicable in other scenarios as well.

Background

Pen type drug delivery devices have application where regular injection by persons without formal medical training occurs. This is increasingly common among patients having diabetes where self-treatment enables such patients to conduct effective management of their disease.

In certain types of medication delivery devices, such as pen type devices, cartridges of medication are used. These cartridges are housed in a cartridge holder or cartridge housing. Such cartridges include a bung or stopper at one end. At the other end of the cartridge, the cartridge comprises a pierceable seal. To dispense a dose of medication from such a cartridge, the medication delivery device has a dose setting mechanism that uses a spindle to move in a distal direction towards the cartridge and to press a distal end of the spindle against the bung. This expels a certain set dose of medication from the cartridge. It is therefore important that the distal end of the spindle does not press on the bung except during normal dose dispense, otherwise some loss of drug may be experienced and the subsequent dose would be below the set value.

One perceived disadvantage of certain known medication delivery devices is that because of the various tolerance differences that may occur during manufacturing (e.g., tolerance differences that may arise during component molding) of the various parts making up the drug delivery device, the combination of these various tolerance differences result in that the cartridge may or may not be held rigidly within the cartridge holder. In other words, the cartridge (and hence cartridge bung) may move away relative to the distal end of the spindle. Therefore, there may be times where the cartridge is not held rigidly within the cartridge holder and can therefore move away from an inner front surface of the cartridge holder.

In addition, a needle assembly must frequently be attached to and removed from the cartridge holder. This allows a double ended needle of the needle assembly to pierce the seal of the cartridge. Frequently attaching and re-attaching needle assemblies may cause the cartridge to move within the cartridge holder.

One advantage of certain typical pen type drug delivery devices is that they are relatively compact. This allows a user to carry around the pen. However, if a user of such pen type delivery devices were to drop or mishandle the device, again movement of the cartridge away from the most distal portion of the cartridge holder could result.

There is, therefore, a general need to take these various perceived issues into consideration when designing either resettable or non-resettable pen type drug delivery devices. Such drug delivery devices would help to prevent unwanted movement of a cartridge contained within a cartridge holder. Specifically, such drug delivery devices would help prevent the cartridge from moving axially relative to the cartridge holder during use of the pen type delivery device: when a needle assembly is attached or removed, or when a user carries around (or drops the drug delivery device) during normal use. Preventing such unwanted movement of the cartridge within the cartridge holder would tend to help insure dispensing accuracy by the device by preventing the spindle distal end from pressing on the bung of the cartridge.

SUMMARY

According to an exemplary arrangement, a non-plastic element for biasing a cartridge in a cartridge housing of a drug delivery device is provided. This non-plastic element does not comprise a coil spring. According to another exemplary arrangement, a self retained element for providing a spring bias to a cartridge in a cartridge holder of a drug delivery device comprises a first member having a shape that allows passage of a spindle of the drug delivery device. A portion of the first member is self retained by an internal surface of the drug delivery device. The self retained element biases the cartridge against an inner surface of the cartridge holder. In one arrangement, this cartridge is a removable cartridge.

According to another arrangement, a method of biasing a cartridge in a drug delivery device cartridge holder is provided. The method comprises the steps of defining an inner end face and a first inner surface of a cartridge holder housing and positioning a cartridge along the first inner surface of the cartridge holder. The method also includes the steps of positioning a self retained biasing element in a dose setting mechanism and connecting the dose setting mechanism to the cartridge holder housing.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which.

DETAILED DESCRIPTION

Figure 1:
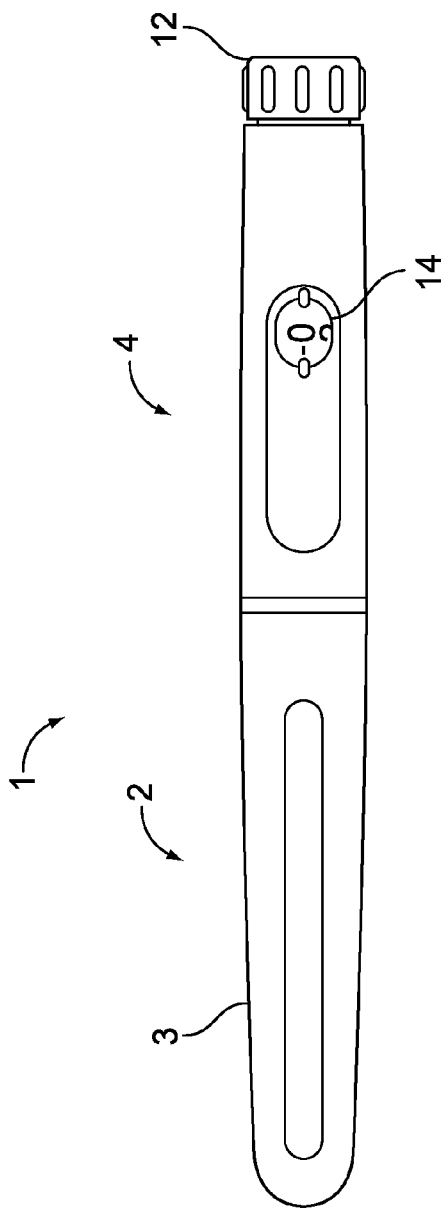
FIG. 1 illustrates an arrangement of the drug delivery device in accordance with the one aspect of the present invention.

Referring to FIG. 1, there is shown a drug delivery device 1 in accordance with a first arrangement of the present invention. The drug delivery device 1 comprises a housing having a first cartridge retaining part 2, and dose setting mechanism 4. The drug delivery device may be a non-resettable drug delivery device (i.e., a reusable device) or alternatively a resettable drug delivery device (i.e., a non-reusable device). A first end of the cartridge retaining means 2 and a second end of the dose setting mechanism 4 are secured together by connecting features. For non-resettable devices, these connecting features would be permanent and for resettable devices, these connecting features would be releasable.

In this illustrated arrangement, the cartridge retaining means 2 is secured within the second end of the dose setting mechanism 4. A removable cap 3 is releasably retained over a second end or distal end of a cartridge retaining part or cartridge housing. The dose setting mechanism 4 comprises a dose dial grip 12 and a window or lens 14. A dose scale arrangement 16 is viewable through the window or lens 14. To set a dose of medication contained within the drug delivery device 1, a user rotates the dose dial grip 12 such that a dialed dose will become viewable in the window or lens 14 by way of the dose scale arrangement 16.

Figure 2:
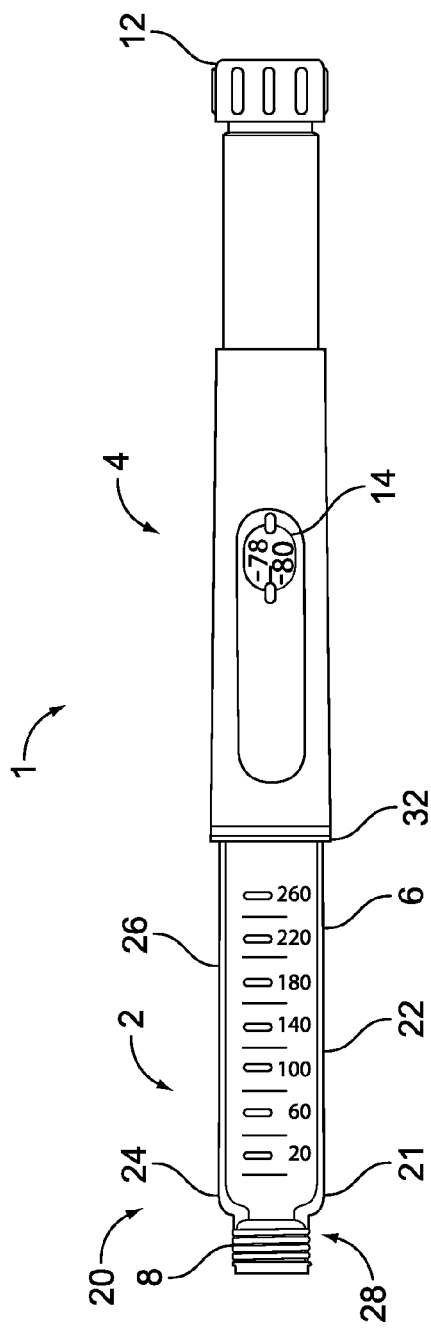
FIG. 2 illustrates the drug delivery device of FIG. 1 with a cap removed and showing a cartridge holder containing a biased cartridge.

FIG. 2 illustrates the medical delivery device 1 of FIG. 1 with the cover 3 removed from a distal end 20 of the medical delivery device 1. This exposes the cartridge housing 6. As illustrated, a cartridge 22 from which a number of doses of a medicinal product may be dispensed, is provided in the cartridge housing 6. Preferably, the cartridge 22 contains a type of medicament that must be administered relatively often, such as once or more times a day. One such medicament is either long acting or short acting insulin or an insulin analog. The cartridge 22 comprises a bung or stopper (not illustrated in FIG. 2) that is retained near a second end or a proximal end 32 of the cartridge 22.

The cartridge housing 6 has a distal end 24 and a proximal end 26. Preferably, the cartridge distal end 24 of the cartridge housing 6 comprises a groove 8 for attaching a removable needle assembly however other needle assembly connection mechanisms could also be used. If the drug delivery device 1 comprises a resettable device, the cartridge proximal end 26 is removably connected to the dose setting mechanism 4. In one preferred embodiment, cartridge housing proximal end 26 is removably connected to the dose setting mechanism 4 via a bayonet connection. However, as those of ordinary skill in the art will recognize, other types of removable connection methods such as threads, partial threads, ramps and detents, snap locks, snap fits, and luer locks may also be used.

The cartridge housing 6 further comprises an inner end face 28 near the first end or distal end 24 of the cartridge housing 6. Preferably, in order to maintain dose accuracy, the cartridge 22 is pressed up against or abuts this inner end face 28. In order to achieve this abutment, as will be discussed in greater detail below, the drug delivery device 1 comprises a biasing mechanism or biasing means (e.g., a non-coiled spring element) that biases the cartridge 22 against this inner end face 28. In one preferred arrangement, this biasing means comprises a self retained spring like member that is releasably connected to an inner or outer housing of the dose setting mechanism 4. By self retained, it is meant that no other component part is required to retain the biasing mechanism to the drug delivery device.

As previously mentioned, the dose setting mechanism 4 of the drug delivery device illustrated in FIG. 2 may be utilized as a reusable drug delivery device. (i.e., a drug delivery device that can be reset) Where the drug delivery device 1 comprises a reusable drug delivery device, the cartridge 22 is removable from the cartridge housing 6. The cartridge 22 may be removed from the device 1 without destroying the device 1 by merely having the user disconnect the dose setting mechanism 4 from the cartridge housing 6.

In use, once the removable cap 3 is removed, a user can attach a suitable needle assembly to the groove 8 provided at the distal end 24 of the cartridge housing 6. Such needle assembly may be screwed onto a distal end 24 of the housing 6 or alternatively may be snapped onto this distal end 24. After user, the replaceable cap 3 may be used to re-cover the cartridge housing 6. Preferably, the outer dimensions of the replaceable cap 3 are similar or identical to the outer dimensions of the dose setting mechanism 4 so as to provide an impression of a unitary whole when the replaceable cap 3 is in position covering the cartridge housing 6 when the device is not in use.

Figure 3:
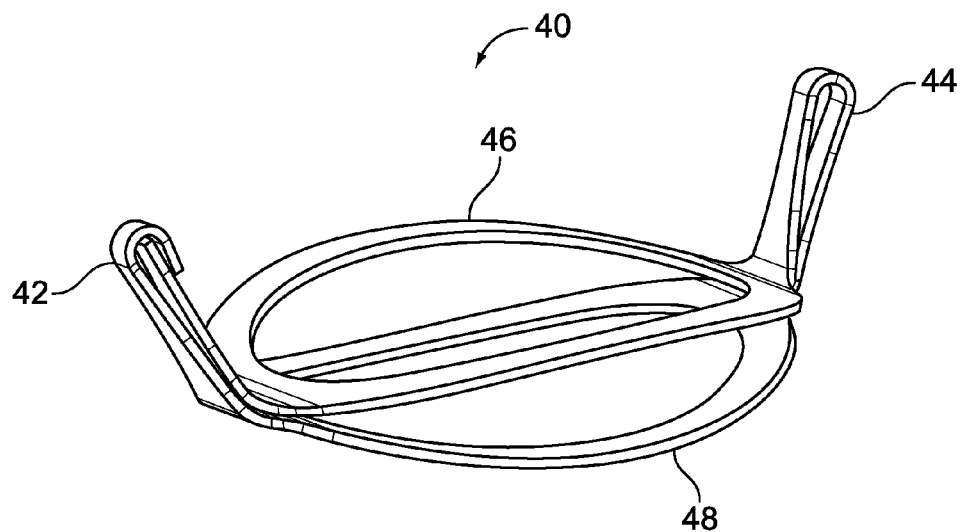
FIG. 3 illustrates a perspective view of a biasing element that may be used to bias the cartridge contained in the cartridge holder of the drug delivery device illustrated in FIG. 2.

FIG. 3 illustrates a perspective view of a biasing member 40 that may be used to bias the cartridge 22 contained in the cartridge housing 6 of the drug delivery device 1 illustrated in FIGS. 1 and 2. In one preferred arrangement, the biasing member 40 is assembled between the cartridge 22 and the dose setting mechanism 4 of a drug delivery device 1. In this position, the biasing member 40 biases the cartridge 22 in an axial direction so that the distal end 21 of the cartridge 22 remains up against the inner end face 28 of the cartridge housing 6.

Using the biasing member 40 between the dose setting mechanism 4 and the cartridge holder 6 results in certain perceived advantages. First, the biasing member 40 will tend to prevent the cartridge 22 from moving axially relative to the cartridge housing 6 when a needle assembly is connected to or disconnected from the distal end 24 of the cartridge housing 6. Second, the biasing member 40 will also help prevent the cartridge 22 from moving axially relative to the cartridge housing 6 when a user handles the device or inadvertently drops the drug delivery device 1. Third, because of the flexible nature of the biasing mechanism, the biasing mechanism 40 will tend to hold the cartridge 22 adjacent the inner end face 28 of the cartridge housing 6 even where a range of manufacturing tolerances between the various component parts is experienced. This will help to ensure dose setting and dose administration accuracy of the drug delivery device 1.

Returning to FIG. 3, preferably, the biasing member 40 comprises a first connection side loop 42 and a second connection side loop 44. These connection side loops 42 and 44 are disposed at opposite ends of the biasing member 40. These side loops 42, 44 are flexible and allow the biasing member 40 to be assembled into a distal end of a dose setting mechanism, such as mechanism 4 and be self retained. The biasing member 40 further comprises an upper wave spring 46 and a lower wave spring 48. Both wave springs 46, 48 have inner diameters and outer diameters that are essentially equal. The upper wave spring 46 and the lower wave spring 48 illustrated in FIG. 3 are shown in an uncompressed or unbiased state. In this state, the upper wave spring 46 is flexing in a proximal direction and the lower wave spring 48 is flexing in a distall direction relative to the connection side loops. Unlike certain conventional coil springs, when the biasing mechanism 40 is in a biased state or is in a compressed state, the biasing mechanism has a relatively small height, in the order of only approximately 1.2+/−0.7 mm. The biasing member 40 has also been designed so that it is self retained in the dose setting mechanism 4 using two small side apertures into which side loops 42, 44 lock when assembled into the dose setting mechanism 4.

Figure 4:
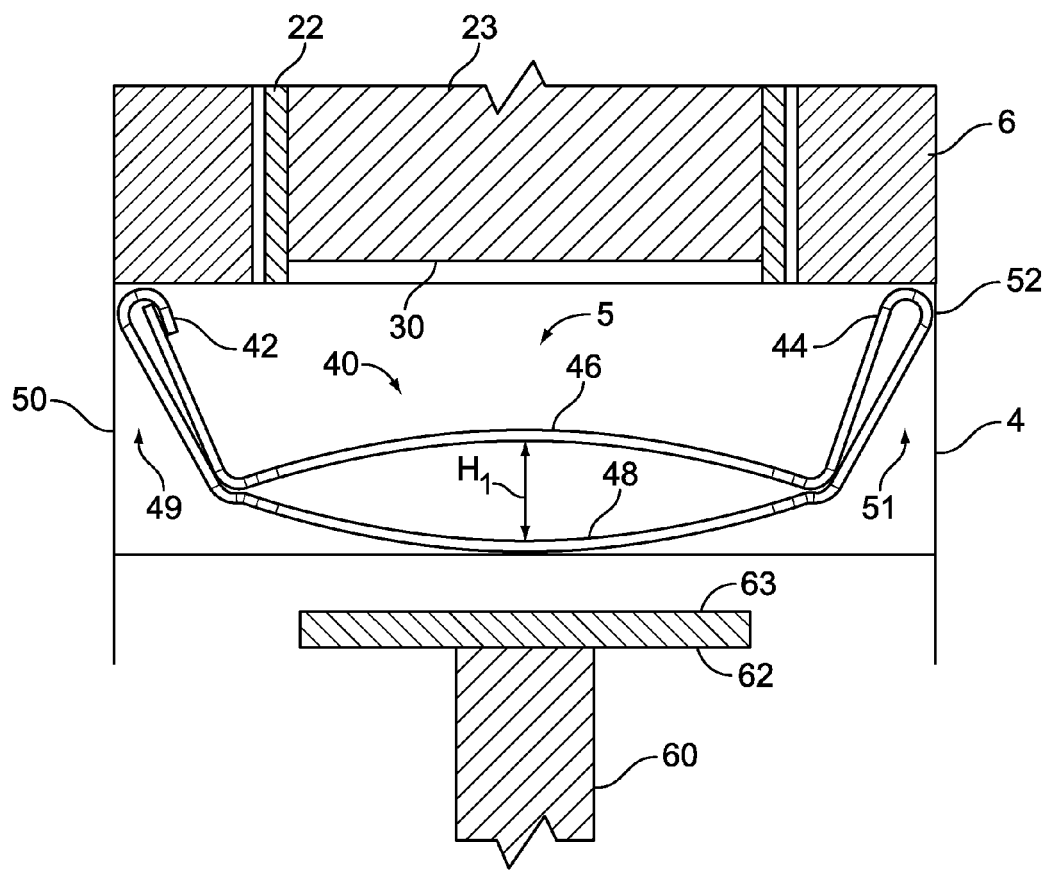
FIG. 4 illustrates one arrangement for mounting the biasing element illustrated in FIG. 3 in a drug delivery device, such as the drug delivery device illustrated in FIGS. 1-2.

FIG. 4 illustrates one arrangement for assembling the biasing member 40 in the drug delivery device 1 illustrated in FIGS. 1-2. As illustrated in FIG. 4, the cartridge housing 6 is shown partially connected to the dose setting mechanism 4 and the biasing mechanism is in an uncompressed state. If the cartridge housing 6 were fully connected to the dose setting mechanism 4, the cartridge 22 would act on the upper wave spring 46 so as to result in both the upper and lower wave springs 46, 48 being in a compressed or biased state. (see, e.g., FIG. 8). However, for ease of explanation, FIG. 4 merely illustrates the cartridge housing 6 and the dose setting mechanism in a partially connected position.

When the biasing mechanism 40 is assembled within the dose setting mechanism 4, the first connecting side loop 42 flexes inwards towards an internal cavity 5 of the dose setting mechanism 4. The flexing nature of the first side loop 42 allows the loop 42 to engage a first aperture 49 in a side wall 50 of a housing of the dose setting mechanism 4. Similarly, the second connecting side loop 44 also flexes inwards towards the internal cavity 5 of the dose setting mechanism internal cavity 5. This second connecting side loop 44 engages a second aperture 51 in a second side wall 52 of a housing of the dose setting mechanism 4. In this uncompressed or unbiased state of biasing mechanism 40, a difference in height between the upper wave spring 46 and the lower wave spring 48 has been designated in FIG. 4 by H1.

Figure 5:
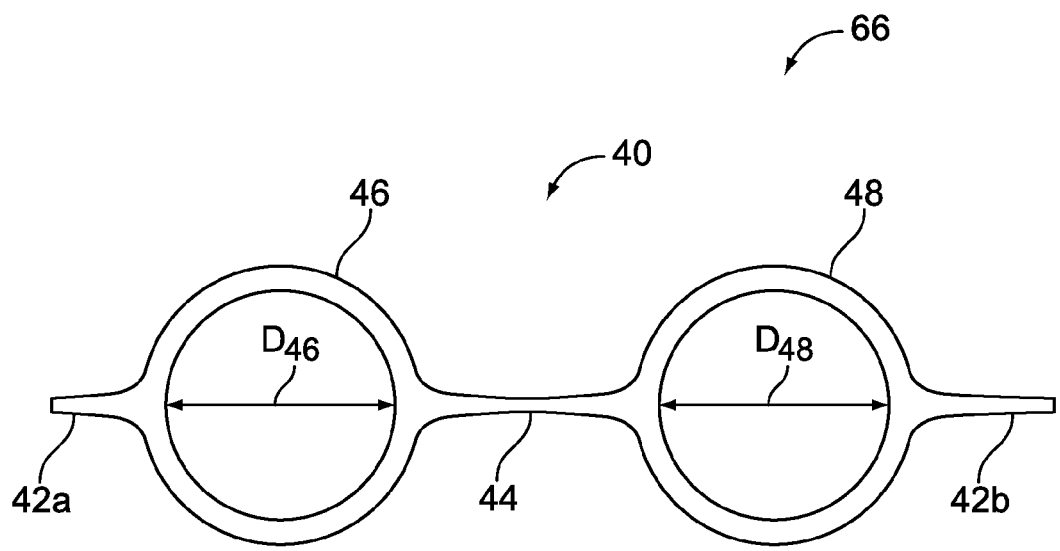
FIG. 5 illustrates a flat profile of the biasing element illustrated in FIG. 3.

The biasing mechanism 40 can be retained in the housing whose internal diameter is just slightly larger than the outer diameter of the cartridge 22. More preferably, the biasing mechanism 40 can be assembled over a spindle whose maximum outer diameter is slightly less than an inner diameter of the cartridge 22. For example, in FIG. 4, the dose setting mechanism 4 comprises a spindle 60 for acting on a proximal surface 30 of bung 23 of a cartridge 22 so that medicine can be expelled from the cartridge 22. The spindle 60 may comprise a spindle bearing 62 near a distal end of the spindle. The spindle bearing 62 comprises a spindle bearing surface 63 for acting on the proximal surface 30 of the bung 23. The biasing mechanism 40 has an inner diameter that is slightly larger than an outer diameter of the spindle bearing 62 or spindle 60 so that an assembled biasing mechanism 40 does not impede movement of this spindle 60 or the spindle bearing 62 during use of the drug delivery device. (i.e., during dose administration or during drug delivery device reset). FIG. 5 illustrates a flat profile 66 of the biasing mechanism 40 illustrated in FIG. 3. As illustrated in FIG. 5, the biasing member 40 comprises a self-contained part or a single unitary part. This self contained member comprises a first member and a second member that are flexibly coupled to one another. The first member comprises a portion 46 having an inner diameter designated in FIG. 5 by D46. The second member comprises a portion 48 having an inner diameter designated in FIG. 5 by D48. The flexible nature of the first and second members allow these members to be manipulated or bent or folded over one another to form the biasing mechanism 40 illustrated in FIG. 3. In one preferred arrangement, the first and second portions 46, 48 comprise circular members however those of skill in the art will recognize other shapes may be utilized as well.

Preferably, once the biasing mechanism 40 is in a folded state, the first member 46 engages the second member 48 to form a first connection side loop 42. In addition, the inner diameter D46 is generally equal to the inner diameter D48 of the second member. This may be seen from FIG. 6.

Figure 6:
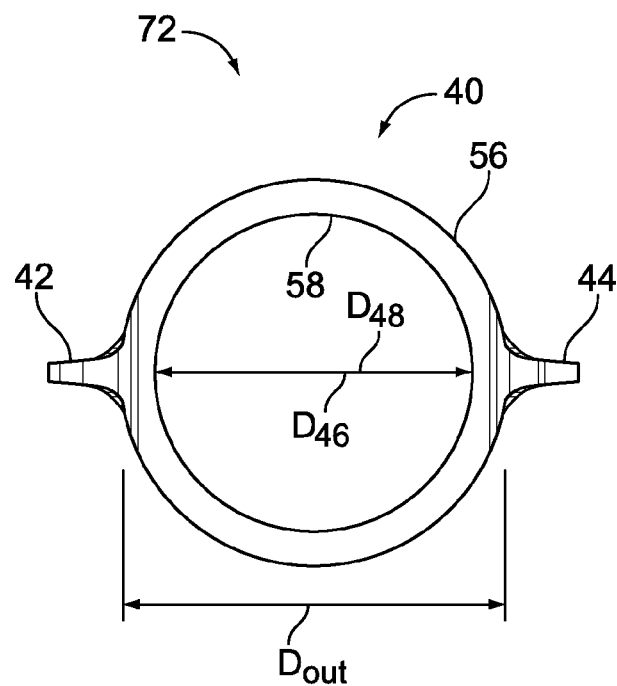
FIG. 6 illustrates a folded profile of the biasing element illustrated in FIG. 5.

FIG. 6 illustrates a folded profile 72 of the biasing means 40 illustrated in FIG. 3. As can be seen from this folded profile 72, when the first member 46 and second member 48 are folded over one another, the biasing means will now have an inner diameter and an outer diameter. Preferably, the inner diameter of the biasing mechanism 40 will be sized to be larger in size or roughly the same size as the inside diameter of the cartridge 22. In addition, the outside diameter 56 identified as Dout of the biasing mechanism 40 will be sized to be smaller or roughly the same size as the outside diameter of the cartridge 22.

Figure 7:
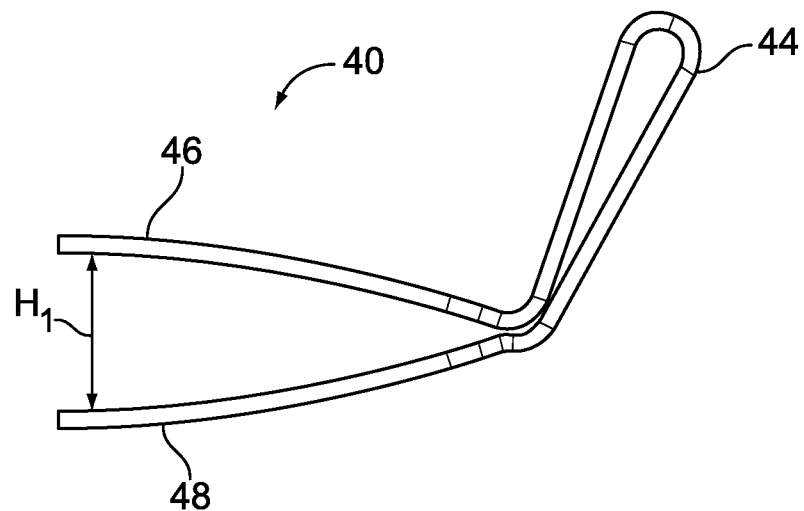
FIG. 7 illustrates one perspective view of a folded profile of the biasing element illustrated in FIG. 3 in a no load state or an uncompressed state.

FIG. 7 illustrates a partial side view 74 of the folded profile 72 of the biasing mechanism 40 illustrated in FIG. 3. In this partial side view 74, the biasing mechanism 40 is illustrated in a no load state. That is, where the biasing mechanism 40 is not biasing a cartridge similar to that illustrated in FIG. 4. In this unbiased state, the upper wave spring of the biasing mechanism will have a first dimension associated with an uncompressed state and the lower wave spring will have a first dimension associated with this uncompressed state. The difference in height between these two dimensions is represented by the height H1.

Figure 8:
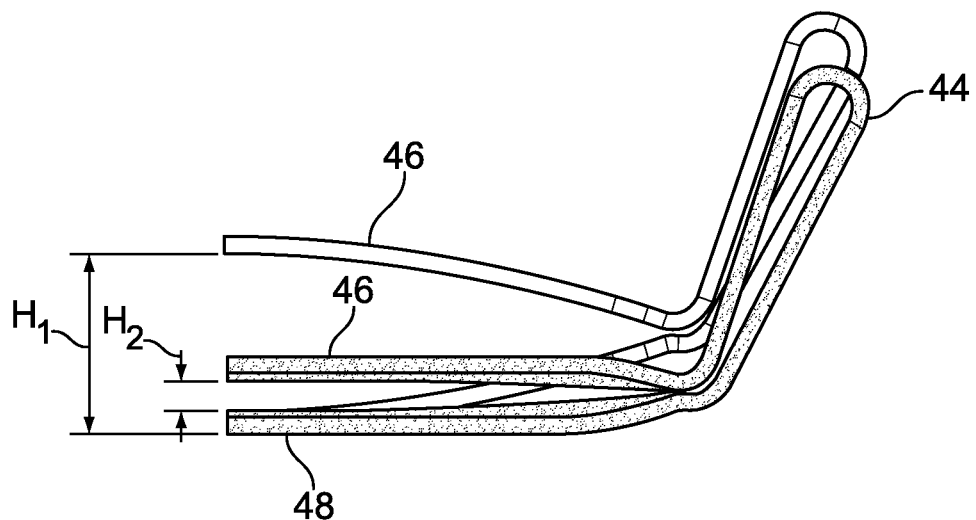
FIG. 8 illustrates one perspective view of a folded profile of the biasing element illustrated in FIG. 3 in a loaded or a compressed state.

FIG. 8 illustrates a folded profile of the biasing means 40 illustrated in FIG. 3 in a compressed state: where the biasing mechanism 40 is biasing a cartridge. In this bent state, the upper wave spring of the biasing mechanism will have a second or different dimension than in the uncompressed state. (Cf., FIG. 7). Similarly, the lower wave spring will have a second or different dimension than in the uncompressed state. (Cf., FIG. 7). The difference in height between the upper wave spring and the lower wave spring in this compressed state is represented by the height H2.

In one preferred arrangement, the difference in height between the uncompressed state H1 and the compressed state H2 of the biasing mechanism 40 will be greater than approximately 0.5 millimeters, and preferably less than approximately 4 millimeters. One advantage of this arrangement is that this low height H2 allows for having a shorter (and less obtrusive) drug delivery device, an advantage for certain users that must carry their pen type drug delivery devices with them throughout the day.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A biasing element configured for biasing a cartridge in a cartridge housing of a drug delivery device, said cartridge housing configured to be secured to a dose setting mechanism, wherein said cartridge comprises a bung at a first end of said cartridge and a pierceable seal at a second end of said cartridge; wherein the biasing element comprises a first connection side loop and a second connection side loop flexibly coupled to said first connection side loop, wherein said first and second connection side loops are disposed at opposite ends of said biasing element and are flexible in a direction radial to a longitudinal axis of said cartridge housing such that at least one portion of said biasing element is configured to be self retained by an internal surface of said drug delivery device, and wherein said biasing element resides in a compressed state when biasing said cartridge in said cartridge housing.

2. The invention of claim 1 wherein said biasing element comprises:
   a first member; and
   a second member folded over said first member,
   said first member having a shape to allow passage of a spindle of said drug delivery device during dose administration of said drug delivery device.

3. The invention of claim 2 wherein a portion of said first member is self retained by an internal surface of said drug delivery device.

4. The invention of claim 2 wherein a portion of said first member is self retained by an internal surface of a dose setting mechanism of said drug delivery device.

5. The invention of claim 1 wherein when said biasing element is compressed, said biasing element compresses to a height of approximately 0.5 millimeters.

6. The invention of claim 1 wherein said cartridge housing comprises a distal end, said distal end used for connecting a needle assembly.

7. The invention of claim 6 wherein when the needle assembly is connected or removed from said distal end, said biasing element prevents said cartridge from moving in a proximal direction in said cartridge housing.

8. The invention of claim 1 wherein said biasing element biases said cartridge against an interior cartridge holder surface.

9. The invention of claim 1 wherein said biasing element comprises:
   a first dimension associated with an uncompressed state when said biasing element is not biasing said cartridge; and
   a second dimension associated with a compressed state when said biasing element is biasing said cartridge,
   such that a difference between said first dimension and said second dimension is less than approximately 4 millimeters.

10. The invention of claim 1 wherein said biasing element comprises
    an upper wave spring, and
    a lower wave spring flexibly coupled to said upper wave spring.

11. The invention of claim 1 wherein said biasing element comprises a non-plastic element.

12. The invention of claim 1, wherein said first connection side loop and said second connection side loop engaging an internal surface of said drug delivery device for self-retention within said drug delivery device.

* * * * *